United States Patent [19]

Perry

[11] Patent Number: Plant 6,863

[45] Date of Patent: Jun. 20, 1989

[54] ROSE PLANT NAMED 'BURWORLD'

[75] Inventor: Anthony Perry, Hemet, Calif.

[73] Assignee: Co-Operative Rose Growers, Inc., Tyler, Tex.

[21] Appl. No.: 168,499

[22] Filed: Mar. 15, 1988

[51] Int. Cl.[4] ..... A01H 5/00

[52] U.S. Cl. ..... Plt./12

[58] Field of Search ..... Plt./12

*Primary Examiner*—James R. Feyrer
*Attorney, Agent, or Firm*—Vincent G. Gioia

[57] ABSTRACT

A new hybrid tea rose variety of vibrant bicolored red and yellow coloring of good exhibition form.

1 Drawing Sheet

1

The present invention relates to a new and distinct variety of rose plant of the hybrid tea rose class, which was originated by my crossing as seed parent the rose known as "First Prize" and the rose known as "Gold Glow" as pollen parent. The new rose is known by the denomination "Burworld".

Among the novel characteristics possessed by this new variety which distinguish it from its parents and all other varieties of which I am aware are vibrant, red and yellow bicolored, high centered, singly borne blooms. Asexual reproduction by budding of the new variety as performed in Smith County, Tex., shows that the foregoing and other distinguishing characteristics come true to form and are established and transmitted through succeeding propagations.

The new and improved rose variety which I have developed is an unusually fine hybrid tea rose with singly-borne blooms of high centered, excellent hybrid tea form. The flowers are of medium petalage and have a slight fragrance. The brilliant coloring holds well upon aging.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horicultural Society Colour Chart (R.H.S.C.C.). The terminology used in color description herein refers to plate numbers in the aforementioned color chart, e.g., "50A" is plate 50A of The Royal Horticultural Society Colour Chart.

Parentage: Seedling.
*Seed parent.*—"First Prize".
*Pollen parent.*—"Gold Glow".
Class: Hybrid tea.

The following observations are made of specimens grown outdoors in Smith County, Tex. during the month of October.

FLOWER

Blooming habit: Continuous.

A. Bud:
(1) *Size.*—Medium.
(2) *Form.*—Ovoid.

2

(3) *Color.*—When sepals first divide — near 50A. When petals begin to unfurl — near 19B and near 51B.
(4) *Sepals.*—Simple, longer than bud.
(5) *Peduncle.*—Length — long. Aspect — straight. Strength — erect. Color — reddish green 182A.

B. Bloom:
(1) *Size.*—Average size when fully expanded — about $4\frac{1}{2}$ to $4\frac{3}{4}$ inches.
(2) *Borne.*—Primarily singly.
(3) *Form.*—High centered, exhibition form, outer petals reflex to points.
(4) *Petalage.*—Number of petals under normal conditions — about 30.
(5) *Color.*—After sepals fall, flowers open into beautiful red and yellow bicolored exhibition blooms. Petal top surfaces are predominantly red, near 44A to 44B, blending toward lower petal segments to deep yellow near 16A, at point of petal attachment. Petal undersurface is near buttercup yellow 16C but includes deeper tones near 16A and 16B through near 15D. Both red and yellow colored sections show veining and washing of darker and lighter tones.

C. Petals:
(1) *Texture.*—Thick.
(2) *Appearance.*—Inside velvety with veining and outside satiny.
(3) *Form.*—Acuminate.
(4) *Arrangement.*—Regularly arranged.
(5) *Petaloids in center.*—Few.
(6) *Persistence.*—Average.
(7) *Fragrance.*—Slight.
(8) *Lasting quality.*—Average.

REPRODUCTIVE ORGANS

A. Stamens, filaments and anthers:
(1) *Arrangement.*—Regular.
(2) *Color.*—Orange to orange red.

B. Pollen:
*Color.*—Yellow.

C. Styles: Even, medium.

D. Stigmas:
*Color.*—Cream colored.

E. Hips:
*Shape.*—Globular.
*Size.*—Medium.
*Color.*—Orange yellow.
*Do seeds protrude?*—No.

PLANT

A. Form: Upright.
B. Growth: Vigorous.
*Height attained.*—About 5 feet.
C. Foliage: Compound 5 to 7 leaflets.
(1) *Size.*—Medium.
(2) *Quantity.*—Abundant.
(3) *Color.*—New foliage: Upper side — purplish green. Under side — purplish green. Old foliage: Upper side — near 147B. Under side — near 148A.
(4) *Shape.*—Ovoid, acuminate.
(5) *Texture.*—Upper side is leathery and under side is dull.
(6) *Edge.*—Serrated.
(7) *Serration.*—Simple.
(8) *Leaf stem.*—Color — light green. Under side — light green.
(9) *Stipules.*—Medium.

(10) *Resistance to disease.*—Blackspot — good. Mildew — good. Rust — good.
D. Wood:
(1) *New wood.*—Color — light green. Bark — smooth.
(2) *Old wood.*—Color — dark green. Bark — smooth.
E. Thorns:
(1) *Thorns.*—Quantity (main stalk) — ordinary. On laterals from stalk — average. Form — thin. Length — medium. Color — tan to greenish brown. Position — irregular.
(2) *Prickles.*—Ordinary.
F. Winter hardiness: Average.

I claim:

1. A new and distinct variety of rose plant of the hybrid tea class, substantially as shown and described, characterized particularly by high centered, exhibition form bicolored blooms of attractive red and yellow coloring borne primarily singly to a stem.

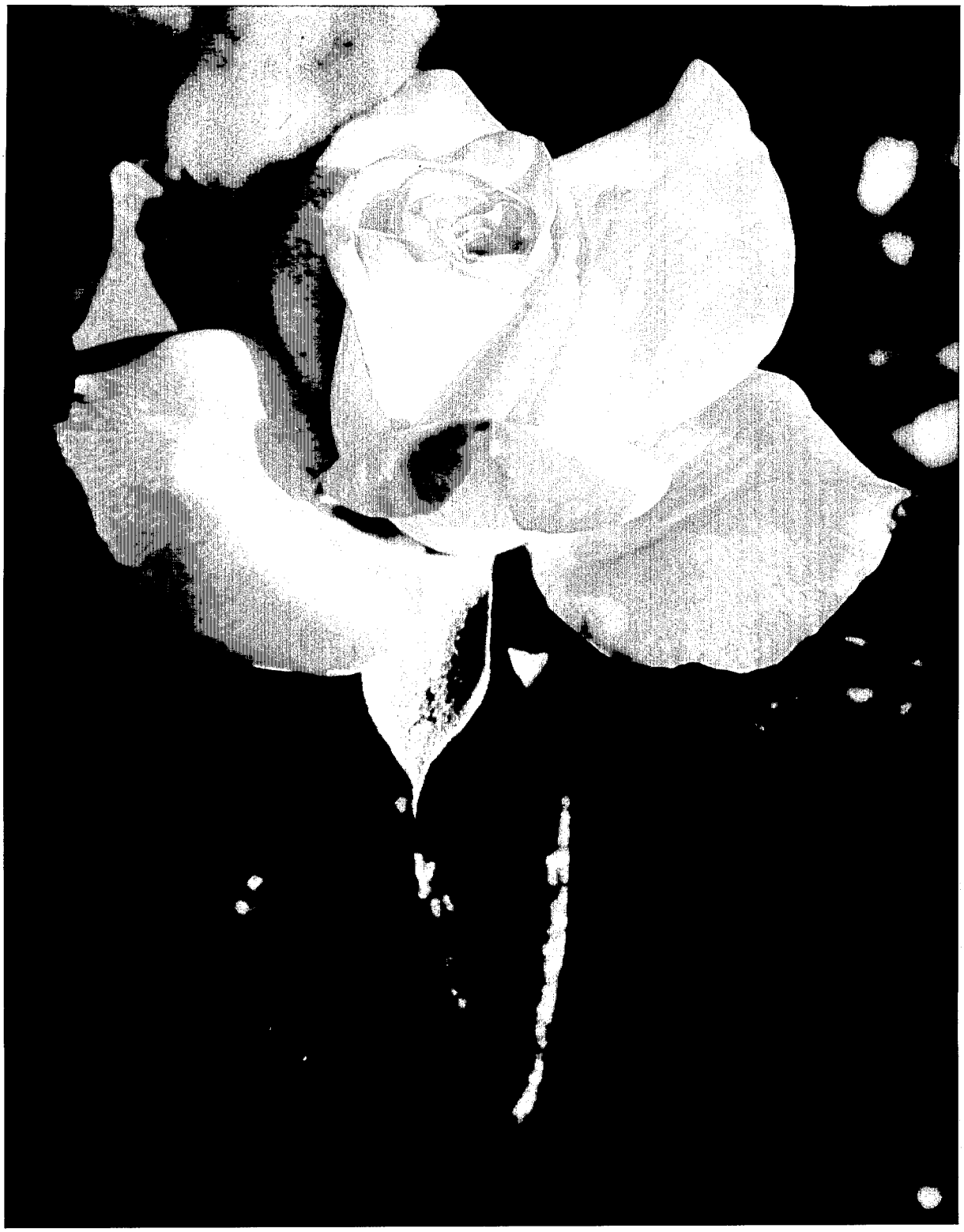

* * * * *